United States Patent [19]

Makino et al.

[11] Patent Number: 4,729,895

[45] Date of Patent: Mar. 8, 1988

[54] COMPOSITION FOR SOLID PHARMACEUTICAL PREPARATIONS OF ACTIVE VITAMINS $D_3$ AND PROCESS FOR PREPARATION THEREOF

[75] Inventors: Yuji Makino; Yoshiki Suzuki, both of Hino, Japan

[73] Assignee: Teijin Limited, Osaka, Japan

[21] Appl. No.: 27,082

[22] Filed: Mar. 16, 1987

Related U.S. Application Data

[63] Continuation of Ser. No. 554,669, Nov. 23, 1983, abandoned.

[30] Foreign Application Priority Data

Feb. 22, 1983 [JP] Japan .................................. 58-26898

[51] Int. Cl.$^4$ .......................... A61K 9/20; A61K 9/26
[52] U.S. Cl. ..................................... 424/465; 424/493; 424/494; 424/495; 424/497; 514/167; 514/960
[58] Field of Search ................. 424/80, 400, 402, 405, 424/22, 23, 465, 471, 494, 495, 497, 493; 514/167, 960

[56] References Cited

U.S. PATENT DOCUMENTS

| | | | |
|---|---|---|---|
| 2,691,619 | 10/1954 | Bavley et al. | 424/80 |
| 3,932,615 | 1/1976 | Ito et al. | 424/80 |
| 3,957,966 | 5/1976 | Valan | 424/80 |
| 4,016,254 | 4/1977 | Seager | 424/80 |
| 4,341,759 | 7/1982 | Bogentoft et al. | 424/19 |

FOREIGN PATENT DOCUMENTS

1081667  6/1982  United Kingdom .

*Primary Examiner*—Douglas W. Robinson
*Attorney, Agent, or Firm*—Sughrue, Mion, Zinn, Macpeak & Seas

[57] ABSTRACT

This invention is concerned with a composition for solid pharmaceutical preparations of active vitamins $D_3$, having the remarkably improved stability of active vitamins $D_3$, and an extremely advantageous process for the preparation thereof from the industrial viewpoint. The composition of this invention is a composition for solid pharmaceutical preparations of active vitamins $D_3$ prepared by forming an outer layer comprising active vitamins $D_3$ and an excipient, which is readily soluble in an organic solvent, around an inner layer comprising an excipient which is slightly soluble in an organic solvent.

4 Claims, No Drawings

COMPOSITION FOR SOLID PHARMACEUTICAL PREPARATIONS OF ACTIVE VITAMINS $D_3$ AND PROCESS FOR PREPARATION THEREOF

This is a continuation of application Ser. No. 554,669 filed Nov. 23, 1983, now abandoned.

FIELD OF THE INVENTION

The present invention relates to a composition for solid pharmaceutical preparations of active vitamins $D_3$ and a process for the preparation thereof. More particularly, the invention relates to a composition for solid pharmaceutical preparations of active vitamins $D_3$ wherein the stability of said active vitamins $D_3$ is remarkably improved and relates to a process for the preparation thereof which is very advantageous from the industrial viewpoint.

DESCRIPTION OF THE PRIOR ART

Active vitamins $D_3$ such as $1\alpha$-hydroxycholecalciferol, $1\alpha,25$-dihydroxycholecalciferol, $1\alpha,24$-dihydroxycholecalciferol, etc. have functions to accelerate the absorption of calcium through the small intestine and also promote the resorption of calcium from the bone and accordingly they are useful as a remedy for treating such diseases as osteoporosis, osteomalacia, rickets, etc.

However, since these active vitamins $D_3$ are all labile and sensitive to heat, light, etc. and also apt to be oxidized, due care should be exercised to store them in a refringerator, shaded place, or inert gas.

It is, therefore, a matter of primary importance to obtain a stable composition of this series of active vitamins $D_3$ for making pharmaceutical preparations.

As a stable pharmaceutical preparations of active vitamins $D_3$, soft capsules containing a vegetable oil solution of active vitamins $D_3$ have hitherto been known (Japanese Patent Application Laid-Open No. 130905/'77). However, soft capsules have their particular drawbacks such as that they are limited in their form and that the process of their preparation is complicated.

As other methods of stabilizing active vitamins $D_3$, a method of forming an inclusion compound with bile acids (Japanese Patent Application Laid-Open No. 69562/'80) and a method of forming a complex with cholesterols (Japanese Patent Application Laid-Open No. 40461/'82) are known. In these methods, the respective compositions are obtained by dissolving active vitamins $D_3$ and bile acids or cholesterols in an organic solvent, followed by the removal of the solvent under reduced pressure.

However, faults have been found with these methods in that part of the obtained composition of active vitamins $D_3$ is resinified during the process of removing the solvent under reduced pressure, thus making the operation intricate, and that it is difficult to obtain a composition of uniform particle size in the process of pulverization after the solvent is removed. Another fault is induced by these faults, making the uniformity of the content of active vitamins $D_3$ in the prepared drug not satisfactory enough when formulated with the obtained composition of active vitamins $D_3$ and other additives.

As a stabilized composition of pharmaceutical preparation, on the other side, Japanese Patent Application Laid-Open No. 135218/'79 has a description of a stabilized composition of prostaglandins E which is obtained by mixing prostaglandins E and a pharmaceutical excipient such as crystalline cellulose, which is slightly soluble in an organic solvent, in an organic solvent in the presence of an organic solventsoluble compound such as polyvinyl pyrrolidone followed by the removal of the organic solvent; however; it has no description at all as to the stabilization of such active vitamins $D_3$ as $1\alpha$-hydroxycholecalciferol, $1\alpha,25$-dihydroxycholecalciferol, etc.

SUMMARY OF THE INVENTION

It is therefore an object of this invention to provide a composition for solid pharmaceutical preparations of active vitamins $D_3$ wherein the stability of said active vitamins $D_3$ is remarkably improved.

It is another object of this invention to provide a process for the preparation of a composition for solid pharmaceutical preparations of active vitamins $D_3$ according to a simple and efficient method whereby a composition uniform in size distribution and homogeneous in active vitamins $D_3$ content can be obtained.

It is a further object of this invention to provide a composition for solid pharmaceutical preparations of active vitamins $D_3$, wherein the stability of said active vitamins $D_3$ to light, heat, oxidation, etc. is remarkably improved.

It is yet another object of this invention to provide a composition of active vitamins $D_3$ which is extremely suited as a composition for making solid preparations such as tablets, powders, granules, etc. of active vitamins $D_3$.

Still other objects of this invention will become apparent from the following detailed description.

These objects and advantages of this invention will be attained by the composition for solid pharmaceutical preparations of active vitamins $D_3$ and the process for the preparation thereof described hereinafter.

To summarize the description, the present invention is concerned with the composition for solid pharmaceutical preparations of active vitamins $D_3$ prepared by forming an outer layer comprising active vitamins $D_3$ and an excipient which is readily soluble in an organic solvent around an inner layer comprising an excipient which is slightly soluble in an organic solvent and also concerned with the process for preparing said composition for solid pharmaceutical preparations of active vitamins $D_3$ characterized by dissolving active vitamins $D_3$ and an organic solvent-soluble excipient in an organic solvent, then by admixing with an excipient which is slightly soluble in an organic solvent, and finally by distilling away the organic solvent.

DETAILED DESCRIPTION OF THE PREFERRED EMBODIMENTS

No limitations have to be specifically considered as to the kind of active vitamins $D_3$ used in this invention and arbitrary selections may be made from any active vitamins $D_3$. As useful active vitamins $D_3$, such $1\alpha$-hydroxy vitamins $D_3$ as $1\alpha$-hydroxycholecalciferol (Steroids, 30, 193 (1977)), $1\alpha,25$-dihydroxycholecalciferol (J. Org. Chem., 40, 2141 (1975)),$1\alpha,24$(R)-dihydroxycholecalciferol (U.S. Pat. No. 4,022,891), $1\alpha,24$(S)-dihydroxycholecalciferol (U.S. Pat. No. 4,022,891), and $1\alpha,24,25$-trihydroxycholecalciferol (Chem. Pharm. Bull., 23, 693 (1975)); such 24- or 25-hydroxy vitamins $D_3$ as 25-hydroxycholecalciferol (Tetrahedron Lett., 1695 (1977)), 24-hydroxycholecalciferol (Biochemical and Biophysical Research Communications, Vol. 62, No.2, 485, 1975), 24,25-dihydroxycholecalciferol (Tetrahedron Lett., 15, (1975)), 25,26-dihydroxycholecalciferol (Tetrahedron Lett., 1097 (1978)), and 25-hydroxy-26,26,26,27,27,27-hexafluorocholecalciferol (International Publication No. WO 83/00335); such 24-oxo vitamins $D_3$ as 24-oxocholecalciferol (Japanese Patent Application Laid-Open No. 100055/'76), 1α-hydroxy-24-oxocholecalciferol (U.S. Pat. No. 939,043), 25-hydroxy-24-oxocholecalciferol (U.S. Pat. No. 121,857), and 1α,25-dihydroxy-24-oxocholecalciferol (U.S. Pat. No. 121,857); and such vitamin $D_3$-26,23-lactones as 25-hydroxycholecalciferol-26,23-lactone (J. Org. Chem., Vol. 46, No. 17, 3423, 1981), 1α,25-dihydroxycholechalciferol-26,23-lactone (U.S. Pat. No. 4,307,231), 25-hydroxycholecalciferol-26,23-peroxylactone (Japanese Patent Application Laid-Open No. 131980/'83), and 1α,25-dihydroxycholecalciferol-26,23-peroxylactone (prepared in the same way as in 25-hydroxycholecalciferol-26,23-peroxylactone), for instance, may be mentioned.

As excipients, slightly soluble in an organic solvent to be used in the present invention, crystalline cellulose, starch, casein, cyclodextrin, lactose, hydroxypropyl starch, dextrin, gelatin, etc., for instance, may be mentioned. These excipients may be used as a mixture of more than one. The foregoing excipients are slightly soluble in an organic solvent and yet they have a property of being water soluble or otherwise water insoluble but absorbent of water. The organic solvents to be used with the excipients, which are slightly soluble in an organic solvent, include such alcoholic solvents as methanol, ethanol, etc.; such solvents of halogenated hydrocarbons as dichloromethane, chloroform, etc.; and such ethereal solvents as diethyl ether, etc. Of all these excipients mentioned above, crystalline cellulose, starch, casein, and cyclodextrin are desirable and crystalline cellulose is especially suited for the present purpose.

As excipients, which are readily soluble in an organic solvent, to be used for the composition in this invention, polyvinyl pyrrolidone, methyl cellulose, ethyl cellulose, hydroxypropyl cellulose, hydroxypropylmethyl cellulose, deoxycholic acid, choresterol, etc., for instance, may be mentioned. These excipients may also be used as a mixture comprising of two or more of them. The organic solvents to be used for an excipient which is readily soluble in an organic solvent mean the same organic solvents that are mentioned above. Of these excipients mentioned above, polyvinyl pyrrolidone and hydroxypropylmethyl cellulose are preferable and polyvinyl pyrrolidone is especially preferable. As for polyvinyl pyrrolidone, polyvinyl pyrrolidone having the molecular weight ranging from 250 to 1,000,000 is preferable, and polyvinyl pyrrolidone having the molecular weight of 1,000 to 700,000 is more preferable.

The composition of the present invention is prepared by forming an outer layer comprising active vitamins $D_3$ and an excipient which is readily soluble in an organic solvent around the inner layer comprising an excipient which is slightly soluble in an organic solvent. In other word, the composition is obtained by forming a particle or a fine granule made up of an excipient which is slightly soluble in an organic solvent as an inner or core layer and then by forming an outer or crust layer made up of a mixture comprising active vitamins $D_3$ and an excipient, which is readily soluble in an organic solvent, by means of allowing said mixture to adhere to or coat the inner layer. It is advisable to make active vitamins $D_3$ disperse uniformly in the excipient, which is readily soluble in an organic solvent, in the outer layer.

The inner layer comprising an excipient which is slightly soluble in an organic solvent is a particle or a fine granule ranging from 40 to 500 micron in size and composes the core of the composition of the present invention. The composition of the present invention is a compound having structure made up of said core and a mixture of active vitamins $D_3$ and an excipient which is readily soluble in an organic solvent, or a dispersion mixture in which active vitamins $D_3$ is dispersed in an excipient which is readily soluble in an organic solvent, wherein the mixture or a dispersion mixture is made to adhere to the surface of said core or to coat the core to form an outer or crust layer.

The amount of an excipient, which is readily soluble in an organic solvent, is preferably in the range of 300 to 1,000,000 times by weight active vitamins $D_3$, and the range of 500 to 100,000 times by weight is especially preferable. The use of an excipient, which is readily soluble in an organic solvent, in vastly great quantities against active vitamins $D_3$ or in the other word the use of active vitamins $D_3$ in extremely small quantities results in the enhancement of the stability of active vitamins $D_3$ in the present invention.

The amount of the excipient, which is slightly soluble in an organic solvent, composing the inner layer is preferably in the range of 1 to 5,000,000 times by weight the excipient, which is readily soluble in an organic solvent, composing the outer layer as one of its ingredients, more preferably in the range of 1 to 10,000 times by weight, and especially preferably in the range of 1 to 100 times by weight.

In the case of the composition prepared according to the present invention, the stability of active vitamins $D_3$ is much improved when said composition is made in the abovementioned form by use of active vitamins $D_3$ as a drug when compared with the case where other drugs such as prostaglandin, etc. are made into compositions of the same structure.

A composition having such structure of the present invention is prepared according to the process mentioned below. Active vitamins $D_3$ and an excipient which is readily soluble in an organic solvent are dissolved in an organic solvent and an excipient, which is slightly soluble in an organic solvent, is admixed thereto and the solvent is thereafter distilled away to give the desired composition.

As the solvents to be used in the process, such alcoholic solvents as methanol, ethanol, and propanol; such solvents of haloganated hydrocarbons as dichloromethane and chloroform; and such ethereal solvents as diethyl ether, etc., for instance, may be mentioned. Of these solvents mentioned above, such alcoholic solvents as methanol, ethanol, etc. are especially preferable. These organic solvents may also be used as a mixture of more than one. Active vitamins $D_3$ and an excipient, which is readily soluble in an organic solvent, are dissolved in such an organic solvent as mentioned above. The ratio of active vitamins $D_3$ to an excipient, which is readily soluble in an organic solvent, to be used is the same as the aforementioned ratio. The amount of an organic solvent to be used is usually 1 to 1,000 times by weight the excipient, which is readily soluble in an organic solvent, preferably 1 to 100 times by weight. Then an excipient, which is slightly soluble in an organic solvent, is added to the obtained solution. At this time, the excipient should be made to exist in the organic solvent in the state of homogeneous suspension.

As aforementioned, the amount of an excipient which is slightly soluble in an organic solvent is preferably 1 to 5,000,000 times by weight an excipient which is readily soluble in an organic solvent, more preferably 1 to 10,000 times by weight, and most preferably 1 to 100 times by weight. After the addition of the excipient, which is slightly soluble in an organic solvent, to the solution, the admixture may be stirred thoroughly. From a consideration of maintaining the stability of active vitamins $D_3$, the series of operations mentioned above should preferably be carried out at a low temperature or room temperature in a dark place.

In the abovementioned procedures, active vitamins $D_3$ and the excipient, which is readily soluble in an organic solvent, solidity to adhere to or cover the surface of the core comprising the excipient, which is slightly soluble in an organic solvent, thus framing up the composition of the present invention having an inner layer comprising an excipient, which is slightly soluble in an organic solvent, and an outer layer comprising active vitamins $D_3$ and an excipient, which is readily soluble in an organic solvent, formed around the said inner layer.

After the abovementioned procedure is over, the used organic solvent is removed by an appropriate method such as a spray-dry method carried out under reduced pressure or atmospheric pressure while heating. The composition for solid pharmaceutical preparations of active vitamins $D_3$ of this invention is obtained in this way.

The abovementioned method proposed by the present invention makes it possible to obtain the desired composition having a uniform size distribution and ingredient content. The method also prevents the resinification of the composition and gives the desired composition very efficiently.

The composition thus obtained can be made into preparations as it is or by addition of publicly known excipient, lubricant, binder, coloring agents, antioxidant, corrigent, etc. The composition of this invention can be made into a powdery preparations by adjusting the particle size properly after the composition is mixed with other additives or as it is. Also, it can be made into tablets by use of a punch, die, press, etc. after it is mixed with other additives or as it is. Furthermore, it can be made into a granules or fine granules by pulverizing and sieving after it is once pressed into slugs. Thus obtained granules and fine granules may fill gelatin hard capsules to make capsules.

Publicly known excipients other than those mentioned above are given below. As excipients, starch, crystalline cellulose, dextrin, lactose, mannitol, sorbitol, calcium phosphate anhydride, etc., for instance, may be mentioned. As lubricants, talc, stearic acid, salt of stearic acid, wax, etc., for instance, may be mentioned. As binders, starch, dextrin, tragacanth, gelatin, polyvinyl pyrrolidone, hydroxypropyl cellulose, polyvinyl alcohol, etc. may be mentioned. As coloring agents, such dyestuffs of tar source as Sunset Yellow, for instance, may be mentioned. As antioxidants, butyl hydroxytoluene (BHT), propyl gellate, butyl hydroxyanisol (BHA), lecithine, α-tocopherol, hydroquinone, ascorbic acid, octyl gallate, and dodecyl gallate, for instance, may be mentioned. As corrigents, citric acid, fumaric acid, menthol, and citrus perfume, for instance, may be mentioned.

The following composition can also be provided according to the present invention. In the aforementioned process, when active vitamins $D_3$ and an excipient, which is readily soluble in an organic solvent, are dissolved in an organic solvent and the solvent is removed from the solution without adding an excipient which is slightly soluble in an organic solvent, a composition is also obtained. The stability of active vitamins $D_3$ is improved to the full extent likewise in this composition, too, which is therefore well suited for making solid pharmaceutical preparations to satisfy the object of the present invention. As excipients, which is readily soluble in an organic solvent, to be used especially in this case, polyvinyl pyrrolidone, methyl cellulose, ethyl cellulose, hydroxypropyl cellulose, and hydroxypropylmethyl cellulose are particularly suited.

Accordingly, the present invention provides a composition for solid pharmaceutical preparations of active vitamins $D_3$ comprising an excipient, which is readily soluble in an organic solvent, selected from a group consisting of polyvinyl pyrrolidone, methyl cellulose, ethyl cellulose, hydroxypropyl cellulose and hydroxypropylmethyl cellulose, and active vitamins $D_3$ and a process for the preparation thereof.

As the excipients to be used here which are readily soluble in an organic solvent, polyvinyl pyrrolidone is especially desirable. Polyvinyl pyrrolidone having the molecular weight ranging from 250 to 1,000,000 is desirable and the one having the molecular weight of 1,000 to 700,000 is especially desirable.

The amount of an excipient which is readily soluble in an organic solvent is preferably 300 to 1,000,000 times by weight active vitamins $D_3$, and 500 to 100,000 times by weight is particularly preferable. It is meant from this fact that it is desirable to use an excipient which is readily soluble in an organic solvent in vastly great quantities against active vitamins $D_3$, in other word, to use active vitamins $D_3$ in extremely small quantities. The stability of active vitamins $D_3$ in the said composition is further improved. In this invention, it is desirable to have active vitamins $D_3$ dispersed uniformly in the excipient which is readily soluble in an organic solvent.

The composition of the present invention is prepared in the following way. It is prepared by dissolving active vitamins $D_3$ and an excipient, which is readily soluble in an organic solvent, in an organic solvent, followed by the removal of the organic solvent from the solution.

As the organic solvents to be used here, such alcoholic solvents as methanol, ethanol, propanol, etc.; such solvents of halogenated hydroxarbons as dichloromethane and chloroform; and such ethereal solvents as diethyl ether, etc., for instance, may be mentioned. The amount of an organic solvent to be used is usually 1 to 1,000 times by weight the excipient which is readily soluble in an organic solvent, preferably 1 to 100 times by weight. After active vitamins $D_3$ and an excipient which is readily soluble in an organic solvent are dissolved in an organic solvent, it is desirable to stir the solution thoroughly and a series of these procedures had better be carried out at a temperature ranging from a low to room temperature in a dark place.

Thereafter, the removal of the organic solvent gives the composition of the present invention. The organic solvent is usually removed by such a method as a spray-dry method carried out under reduced pressure or atmospheric pressure while heating.

In this way, the composition for solid pharmaceutical preparations of active vitamins $D_3$ proposed by the present invention is obtained and the composition thus obtained contains active vitamins $D_3$ whose stability is improved remarkably.

As described hereinbefore, the composition of this invention can be used in the state as it is or otherwise it can be made into tablets, granules, powders, capsules, etc. in a usual way after it is mixed with a lubricant, binder, coloring matter, etc.

The present invention is described in detail by the following examples.

EXAMPLE 1

1 mg of 1α-hydroxycholecalciferol (1α-OH-$D_3$) was dissolved in 1 ml of ethanol to obtain a solution, which was then added to 100 ml of an ethanol solution in which 10 g of polyvinyl pyrrolidone (molecular weight of about 40,000) had been dissolved, and the mixture was stirred and mixed for 10 minutes. 30 g of crystalline cellulose was added to the obtained solution and the mixture was stirred and mixed for another 10 minutes. Thereafter, ethanol was distilled away under reduced pressure and the residue was dried to give 38.8 g of a composition. The content of 1α-OH-$D_3$ in the composition was 0.0025% by weight.

This composition was kept in storage at 40° C. and the residual percentage of 1α-OH-$D_3$ was examined as time passed. As a control, 1,000-fold corn starch powders of 1α-OH-$D_3$ was used. This control was obtained by adding 1 g of corn starch to a solution prepared by dissolving 1 mg of 1α-OH-$D_3$ in 10 ml of ethanol, followed by the removal of ethanol by distillation under reduced pressure and then by drying. Changes in the residual percentage of 1α-OH-$D_3$ of the composition of this invention were examined as time passed in comparison with the control and the result is shown in Table 1. It is confirmed from Table 1 that the residual percentage of 1α-OH-$D_3$ shows almost no decrease over a long period of time in the composition of the present invention in marked contrast to the control in which 1α-OH-$D_3$ decomposes rapidly.

TABLE 1

| Condition | Time passed | Specimen Composition of this invention | Control |
|---|---|---|---|
| Stability at 40° C. | 30 days | 100% | 30% |
| | 60 days | 99% | 5% |

TABLE 1-continued

| Condition | Time passed | Specimen Composition of this invention | Control |
|---|---|---|---|
| | 90 days | 98% | |

When the composition of this invention obtained in the above preparation was made to contact an iodine vapor, its surface was colored in yellow to brown. It is known that polyvinyl pyrrolidone reacts with iodine to form a yellow to brown compound. On the other hand, crystalline cellulose does not react with iodine at all. It is confirmed from the above fact that the outer layer of the composition of this invention is covered with polyvinyl pyrrolidone.

When the composition of this invention is subjected to ethanol extraction and the solvent was distilled away from the extract separated from the residue, polyvinyl pyrrolidone was recovered. And it was confirmed that 1α-OH-$D_3$ was contained in the recovery when subjected to high pressure liquid chromatography.

It has been made clear from the fact mentioned above that the composition of the present invention has crystalline cellulose as an inner layer and polyvinyl pyrrolidone as an outer layer in which 1α-OH-$D_3$ is contained.

EXAMPLES 2-9

The compositions of the present invention were obtained according to the same method as Example 1, wherein 1 mg each of various active vitamins $D_3$ and various excipients which are slightly soluble in an organic solvent were used. These compositions were kept in storage at 40° C. to examine the stability of active vitamins $D_3$ and corn starch were also prepared as controls and the stability of active vitamins $D_3$ contained therein was also examined likewise. The result of the examination is shown in Table 2.

TABLE 2

| Example | Active vitamin $D_3$ | Excipient slightly soluble in organic solvent Kind | Quantity (g) | Stability (residual percentage of active vitamin $D_3$) 30 days | 60 days | 90 days | Stability (control) 30 days | 60 days |
|---|---|---|---|---|---|---|---|---|
| 2 | 1α,24-(OH)$_2$—$D_3$ | Crystalline cellulose | 30 | 100 | 99 | 98 | 25 | 4 |
| 3 | 24-OH—$D_3$ | " | 30 | 100 | 99 | 98 | 30 | 5 |
| 4 | 1α-OH—$D_3$ | Corn starch | 30 | 100 | 99 | 98 | 30 | 5 |
| 5 | 1α,24-(OH)$_2$—$D_3$ | " | 30 | 100 | 99 | 98 | 25 | 4 |
| 6 | 24-OH—$D_3$ | " | 30 | 100 | 99 | 98 | 30 | 5 |
| 7 | 1α-OH—$D_3$ | Casein | 30 | 100 | 99 | 98 | 30 | 5 |
| 8 | 1α,24-(OH)$_2$—$D_3$ | " | 30 | 100 | 99 | 98 | 25 | 4 |
| 7 | 24-OH—$D_3$ | " | 30 | 100 | 99 | 98 | 30 | 5 |

EXAMPLES 10-24

The compositions, comprising 1 mg of active vitamins $D_3$ plus 10 g each of various polyvinyl pyrrolidones (outer layer) and 30 g each of various excipients which are slightly soluble in an organic solvent (inner layer), were prepared according to Example 1. These compositions were kept in storage at 40° C. and the residual percentage of active vitamin $D_3$ of the respective compositions was determined 1 month and 2 months later. The result is shown in Table 3.

TABLE 3

| Example | Active vitamin $D_3$ | Polyvinyl pyrrolidone | Inner layer substance | Stability (residual percentage of active vitamin $D_3$) | |
|---|---|---|---|---|---|
| | | | | 1 month later | 2 months later |
| 10 | $1\alpha$-OH—$D_3$ | Polyvinyl pyrrolidone (molecular weight, about 25,000) | Crystalline cellulose | 100 | 99 |
| 11 | " | Polyvinyl pyrrolidone (molecular weight, about 25,000) | Corn starch | 100 | 98 |
| 12 | " | Polyvinyl pyrrolidone (molecular weight, about 25,000) | Casein | 100 | 99 |
| 13 | " | Polyvinyl pyrrolidone (molecular weight, about 160,000) | Crystalline cellulose | 100 | 99 |
| 14 | " | Polyvinyl pyrrolidone (molecular weight, about 160,000) | Corn starch | 100 | 98 |
| 15 | " | Polyvinyl pyrrolidone (molecular weight, about 160,000) | Casein | 99 | 98 |
| 16 | " | Polyvinyl pyrrolidone (molecular weight, about 360,000) | Crystalline cellulose | 100 | 99 |
| 17 | " | Polyvinyl pyrrolidone (molecular weight, about 360,000) | Corn starch | 100 | 99 |
| 18 | " | Polyvinyl pyrrolidone (molecular weight, about 360,000) | Casein | 100 | 99 |
| 19 | $1\alpha,24$-$(OH)_2$—$D_3$ | Polyvinyl pyrrolidone (molecular weight, about 25,000) | Crystalline cellulose | 100 | 98 |
| 20 | " | Polyvinyl pyrrolidone (molecular weight, about 160,000) | Crystalline cellulose | 100 | 98 |
| 21 | " | Polyvinyl pyrrolidone (molecular weight, about 360,000) | Crystalline cellulose | 100 | 98 |
| 22 | 24-OH—$D_3$ | Polyvinyl pyrrolidone (molecular weight, about 25,000) | Crystalline cellulose | 100 | 99 |
| 23 | " | Polyvinyl pyrrolidone (molecular weight, about 160,000) | Crystalline cellulose | 100 | 99 |
| 24 | " | Polyvinyl pyrrolidone (molecular weight, about 360,000) | Crystalline cellulose | 100 | 98 |

EXAMPLE 25

1 mg of $1\alpha$-hydroxycholecalciferol ($1\alpha$-OH-$D_3$) was dissolved in ethanol to make a solution. The solution was then added to 100 ml of a mixed solvent of ethanol and dichloromethane (volume ratio 1:1) containing 10 g of hydroxypropylmethyl cellulose (molecular weight, about 15,000) dissolved therein. This was stirred and mixed thoroughly for 10 minutes. Further, 30 g of crystalline cellulose was added to the solution and stirred and mixed for another 10 minutes. Thereafter, ethanol and dichloromethane were distilled away under reduced pressure and dried to give 38.9 g of the desired composition. The content of $1\alpha$-OH-$D_3$ in the composition was 0.0025% by weight.

This composition was stored at 40° C. and the residual percentage of $1\alpha$-hydroxycholecalciferol was measured 1 month and 2 months later respectively. The result is shown in Table 4. As a control, the composition obtained in Example 1 was used.

TABLE 4

| Condition | Time passed | Specimen | |
|---|---|---|---|
| | | Composition of this invention | Control |
| Stability at 40° C. | 30 days | 99% | 30% |
| | 60 days | 97% | 5% |
| | 90 days | 96% | |

EXAMPLES 26-29

The compositions were prepared according to Example 25, respectively comprising 1 mg of $1\alpha$-hydroxycholecalciferol ($1\alpha$-OH-$D_3$) plus 10 g each of various excipients readily soluble in an organic solvent (outer layer) and 30 g of crystalline cellulose (inner layer). These compositions were kept in storage at 40° C. and the residual percentage of $1\alpha$-OH-$D_3$ was measured 1 month and 2 months later. The result is shown in Table 5.

TABLE 5

| Example | Active vitamin $D_3$ | Excipient readily soluble in organic solvent | Inner layer substance | Stability (residual percentage of active vitamin $D_3$) | |
|---|---|---|---|---|---|
| | | | | 1 month later | 2 months later |
| 26 | $1\alpha$-OH—$D_3$ | Methyl cellulose | Crystalline cellulose | 97 | 95 |
| 27 | " | Hydroxypropyl cellulose | Crystalline cellulose | 96 | 94 |
| 28 | " | Ethyl cellulose | Crystalline cellulose | 97 | 95 |
| 29 | " | Deoxycholic acid | Crystalline cellulose | 95 | 93 |

Comparative Example 1

In the same way as Example 1, 1 mg of prostaglandin $E_1$ was dissolved in 1 ml of ethanol to make a solution.

The solution was added to 100 ml of an ethanol solution containing 10 g of polyvinyl pyrrolidone(molecular weight, about 40,000) dissolved therein. After the mixed solution was stirred for 10 minutes, 30 g of crystallin cellulose was added thereto and the mixture was stirred for 10 minutes. Then ethanol was distilled away under reduced pressure and the residue was dried to obtain 38.7 g of a reaction product. The thermal stability of prostaglandin $E_1$ in the reaction product was compared with the thermal stability of $1\alpha$-OH-$D_3$ in the reaction product of Example 1 of this invention and the result is shown in Table 6. It is confirmend from Table 6 that $1\alpha$-OH-$D_3$ contained in the composition of the present invention is stabilized while prostaglandin $E_1$ in the reaction product prepared in the same way is not stabilized enough.

TABLE 6

| Condition | Time passed | Specimen | |
|---|---|---|---|
| | | Composition of Example 1 (residual percentage of $1\alpha$-OH—$D_3$) | Composition of prostaglandin $E_1$ (residual percentage of prostaglandin $E_1$) |
| Stability at 40° C. | 7 days | 100% | 89% |
| | 14 days | 100% | 81% |
| | 30 days | 100% | 69% |
| | 60 days | 99% | 52% |
| | 90 days | 98% | 40% |

REFERENTIAL EXAMPLE 1

Powder composed of the following additives including the composition of the present invention 5 obtained in Example 1 was prepared and made into tablets, 7 mm in diameter and 2 mm in thickness, with the use of Erweka single punch tableting machine.

| | | |
|---|---|---|
| Composition of this invention | 40.0 | parts by weight |
| Crystalline cellulose | 58.0 | parts by weight |
| Magnesium stearate | 1.0 | part by weight |
| Talc | 1.0 | part by weight |

The obtained tablets contained about 1.0 μg of $1\alpha$-OH-$D_3$ per tablet.

REFERENTIAL EXAMPLE 2

The composition of this invention obtained in Example 1 was mixed with refined sucrose and was then made into granules by admixing corn starch as a binder with the use of a sieve type granule machine. This was granules for preparation of syrups composed of the following ingredients.

| | | |
|---|---|---|
| Composition of this invention | 40.0 | parts by weight |
| Corn starch | 2.0 | parts by weight |
| Refined sucrose | 958.0 | parts by weight |

This granules contained about 1.0 μg of $1\alpha$-OH-$D_3$ per gram.

EXAMPLE 30

A solution was prepared by dissolving 1 mg of $1\alpha$-OH-$D_3$ in 1 ml of ethanol. The solution was added to 100 ml of an ethanol solution containing 1 g of polyvinyl pyrrolidone (molecular weight, about 40,000) dissolved therein and was stirred for 10 minutes. Ethanol was then distilled away from the solution under reduced pressure and the residue was dried to obtain 990 mg of a reaction product. The content of $1\alpha$-OH-$D_3$ of this reaction product was 0.1% by weight.

Thus obtained composition of this invention was stored at 40° C. and the residual percentage of $1\alpha$-OH-$D_3$ was examined as time passed. As a control, 1,000-fold corn starch powders of $1\alpha$-OH-$D_3$ was used. This control was obtained by adding 1 g of corn starch to 10 ml of an ethanol solution containing 1 mg of $1\alpha$-OH-$D_3$ dissolved therein, then distilling away ethanol therefrom under reduced pressure, followed by drying. The result of the examination made to know the residual percentage of $1\alpha$-OH-$D_3$ contained in the composition of this invention as time passed in comparison with the control is shown in Table 7. It is confirmed from Table 7 that the residual percentage of $1\alpha$-OH-$D_3$ shows almost no decrease over a long period of time in the composition of the present invention in marked contrast to the control in which $1\alpha$-OH-$D_3$ decomposes rapidly.

Also, the light stability of $1\alpha$-OH-$D_3$ in the composition of the present invention is described in Table 7. This composition and the abovementioned control were respectively placed in the different transparent glass bottles and were left standing beside the window in the room. The residual percentage of $1\alpha$-OH-$D_3$ in the respective substances was examined as time passed. It was found that the composition of this invention was much stable to light as compared with the control.

Table 7 also shows how $1\alpha$-OH-$D_3$ contained in the composition of this invention is stable to oxygen. In the test, said composition and the abovementioned control was placed in the respective glass tubes and both ends of the glass tubes were stopped up with glass wool. Then oxygen was let pass through the respective glass tubes at a flow rate of 15 ml/min to determine the residual percentage of $1\alpha$-OH-$D_3$ as time passed. It was thus confirmed that the composition of this invention is much more stable to oxygen than the control.

TABLE 7

| Stability | Time passed | Specimen | |
|---|---|---|---|
| | | Composition of this invention | Control |
| Stability to heat | 10 days | 100% | 30% |
| | 20 days | 100% | 5% |
| | 30 days | 99% | — |
| | 60 days | 98% | — |
| Stability to light | 10 days | 100% | 18% |
| | 20 days | 97% | 0% |
| | 30 days | 96% | — |
| | 60 days | 94% | — |
| Stability to oxygen | 10 hours | 100% | 77% |
| | 20 hours | 98% | 62% |
| | 30 hours | 97% | 37% |
| | 60 hours | 95% | 5% |

EXAMPLES 31-33

Several compositions were obtained by use of active vitamins $D_3$ of various kinds according to Example 30. Their stability to heat, light and oxygen was examined and the result is shown in Table 8.

TABLE 8

| Example | Active Vitamin $D^3$ | Stability to heat (%) | | | | Stability to light (%) | | | | Stability to oxygen (%) | | | |
|---|---|---|---|---|---|---|---|---|---|---|---|---|---|
| | | 10 days | 20 days | 30 days | 60 days | 10 days | 20 days | 30 days | 60 days | 10 hours | 20 hours | 30 hours | 60 hours |
| 31 | 1α,24-(OH)$_2$—D$_3$ | 100 | 99 | 98 | 98 | 100 | 98 | 97 | 95 | 100 | 99 | 99 | 95 |
| 32 | 24-OH—D$_3$ | 100 | 100 | 99 | 97 | 100 | 98 | 96 | 96 | 100 | 98 | 97 | 96 |
| 33 | 1α,25-(OH)$_2$—D$_3$ | 100 | 99 | 98 | 97 | 100 | 99 | 97 | 97 | 100 | 98 | 98 | 97 |

EXAMPLES 34–45

The compositions respectively comprising 1 mg of active vitamin D$_3$ and 1 g of polyvinyl pyrrolidone, each component being selected from among the various kinds of its own, were prepared according to Example 30. These compositions were kept in storage at 40° C. and the residual percentage of active vitamin D$_3$ was measured 1 month later and 2 months later. The result is shown in Table 9.

TABLE 9

| Example | Active vitamin D$_3$ | Polyvinyl pyrrolidone | Stability (residual percentage of active vitamin D$_3$) | |
|---|---|---|---|---|
| | | | 1 month later | 2 months later |
| 34 | 1α-OH—D$_3$ | Polyvinyl pyrrolidone (molecular weight, about 25,000) | 100 | 99 |
| 35 | 1,24-(OH)$_2$—D$_3$ | Polyvinyl pyrrolidone (molecular weight, about 25,000) | 99 | 98 |
| 36 | 24-OH—D$_3$ | Polyvinyl pyrrolidone (molecular weight, 25,000) | 100 | 98 |
| 37 | 1α-OH—D$_3$ | Polyvinyl pyrrolidone (molecular weight, about 160,000) | 100 | 99 |
| 38 | 1,24-(OH)$_2$—D$_3$ | Polyvinyl pyrrolidone (molecular weight, about 160,000) | 100 | 97 |
| 39 | 24-OH—D$_3$ | Polyvinyl pyrrolidone (molecular weight, about 160,000) | 99 | 98 |
| 40 | 1α-OH—D$_3$ | Polyvinyl pyrrolidone (molecular weight, about 360,000) | 99 | 99 |
| 41 | 1,24-(OH)$_2$—D$_3$ | Polyvinyl pyrrolidone (molecular weight, about 360,000) | 100 | 98 |
| 42 | 24-OH—D$_3$ | Polyvinyl pyrrolidone (molecular weight, about 360,000) | 99 | 97 |
| 43 | 1α-OH—D$_3$ | Polyvinyl pyrrolidone (molecular weight, about 700,000) | 99 | 98 |
| 44 | 1,24-(OH)$_2$—D$_3$ | Polyvinyl pyrrolidone (molecular weight, 700,000) | 100 | 98 |
| 45 | 24-OH—D$_3$ | Polyvinyl pyrrolidone (molecular weight, about 700,000) | 100 | 99 |

EXAMPLE 46

1 mg of 1α-hydroxycholecalciferol (1α-OH-D$_3$) was dissolved in 1 ml of ethanol to make a solution, which was then added to 100 ml of a mixed solution of ethanol and dichloromethane (volume ratio, 1:1) containing 1 g of hydroxypropylmethyl cellulose (molecular weight, about 15,000) dissolved therein and the mixture was stirred thoroughly for 10 minutes. The solvents were distilled away from the solution under reduced pressure and the residue was dried to obtain 970 mg of a reaction product. The content of 1α-OH-D$_3$ in this reaction product was 0.1% by weight.

The stability of this composition to heat, light, and oxygen was examined according to Example 30 and the result is shown in Table 10. As a control, a composition similar to the one prepared for the same purpose in Example 1 was used.

TABLE 10

| Stability | Time passed | Specimen | |
|---|---|---|---|
| | | Composition of this invention | Control |
| Stability to heat | 10 days | 98% | 30% |
| | 20 days | 96% | 5% |
| | 30 days | 95% | — |
| | 60 days | 94% | — |
| Stability to light | 10 days | 100% | 18% |
| | 20 days | 99% | 0% |
| | 30 days | 97% | — |
| | 60 days | 96% | — |
| Stability to oxygen | 10 hours | 100% | 77% |
| | 20 hours | 96% | 62% |
| | 30 hours | 96% | 37% |
| | 60 hours | 95% | 5% |

EXAMPLES 47–49

The composition respectively comprising 1 mg of 1α-hydroxycholecalciferol (1α-OH-D$_3$) and 1 g each of excipients of various kinds which are readily soluble in an organic solvent were prepared according to Example 46. The stability of thus prepared composition to heat, light, and oxygen was examined. The result is shown in Table 11.

TABLE 11

| Example | Active vitamin D$_3$ | Excipient readily soluble in an organic solvent | Stability to heat (%) | | | | Stability to light (%) | | | | Stability to oxygen (%) | | | |
|---|---|---|---|---|---|---|---|---|---|---|---|---|---|---|
| | | | 10 days | 20 days | 30 days | 60 days | 10 days | 20 days | 30 days | 60 days | 10 hrs. | 20 hrs. | 30 hrs. | 60 hrs. |
| 47 | 1α-OH—D$_3$ | Methyl | 97 | 97 | 94 | 93 | 99 | 98 | 96 | 95 | 98 | 98 | 97 | 95 |

TABLE 11-continued

| Example | Active vitamin $D_3$ | Excipient readily soluble in an organic solvent | Stability to heat (%) | | | | Stability to light (%) | | | | Stability to oxygen (%) | | | |
|---|---|---|---|---|---|---|---|---|---|---|---|---|---|---|
| | | | 10 days | 20 days | 30 days | 60 days | 10 days | 20 days | 30 days | 60 days | 10 hrs. | 20 hrs. | 30 hrs. | 60 hrs. |
| 48 | $1\alpha\text{-OH}-D_3$ | Hydroxypropyl cellulose | 96 | 96 | 95 | 93 | 100 | 97 | 95 | 94 | 97 | 97 | 96 | 96 |
| 49 | $1\alpha\text{-OH}-D_3$ | Ethyl cellulose | 97 | 96 | 95 | 94 | 98 | 96 | 95 | 95 | 98 | 98 | 95 | 94 |

What we claim is:

1. A solid pharmaceutical, composition of active vitamins $D_3$ having improved stability comprising:
   (a) an outer layer comprising an active vitamin $D_3$ and an excipient which is readily soluble in an organic solvent and containing from 500 to 100,000 parts by weight of said excipient per 1 weight part of active vitamin $D_3$, said excipient which is readily soluble in an organic solvent being selected from the group consisting of polyvinyl pyrrolidone, methyl cellulose, ethyl cellulose hydroxypropyl cellulose, hydroxypropylmethyl celluose, and mixtures thereof and
   (b) a core material comprising an excipient which is slightly soluble in an organic solvent, said excipient which is slightly soluble in an organic solvent being selected from the group consisting of crystalline cellulose, lactose, and mixtures thereof; said core material containing from 1 to 100 parts by weight of said excipient which is slightly soluble in an organic solvent per 1 weight part of said excipient in the outer layer which is readily soluble in an organic solvent.

2. A solid pharmaceutical composition of active vitamins $D_3$ having improved stability according to claim 1, wherein said active vitamin $D_3$ is at least one of $1\alpha$-hydroxy vitamin $D_3$, 24- or 25-hydroxy vitamin $D_3$, 24-oxo vitamin $D_3$, or a vitamin $D_3$-26,23-lactone.

3. A solid pharmaceutical composition of active vitamins $D_3$ having improved stability comprising:
   (a) an outer layer comprising an active vitamin $D_3$ and an excipient which is readily soluble in an organic solvent and containing from 500 to 100,000 parts by weight of said excipient per 1 weight part of active vitamin $D_3$, said excipient which is readily soluble in an organic solvent being selected from the group consisting of polyvinyl pyrrolidone, methyl cellulose, ethyl cellulose, hydroxypropyl cellulose, hydroxypropylmethyl cellulose, and mixtures thereof and
   (b) a core material comprising an excipient which is slightly soluble in an organic solvent, said excipient which is slightly soluble in an organic solvent being selected from the group consisting of crystalline cellulose, lactose, and mixtures thereof; said core material containing from 1 to 10,000 parts by weight of said excipient which is slightly soluble in an organic solvent per 1 weight part of said excipient in the outer layer which is readily soluble in an organic solvent.

4. A solid pharmaceutical composition of active vitamins $D_3$ having improved stability according to claim 3, wherein said active vitamin $D_3$ is at least one of $1\alpha$-hydroxy vitamin $D_3$, 24- or 25-hydroxy vitamin $D_3$, 24-oxo vitamin $D_3$, or vitamin $D_3$-26,23-lactone.

* * * * *